US006935889B2

(12) United States Patent
Picardo et al.

(10) Patent No.: US 6,935,889 B2
(45) Date of Patent: Aug. 30, 2005

(54) ELECTRODE-PAD PACKAGE THAT IS REMOVABLE FROM AN ELECTRODE-PAD LEAD AND METHOD FOR OPENING THE PACKAGE

(75) Inventors: Anthony G. Picardo, Tacoma, WA (US); Christine Janae, Seattle, WA (US); Thomas Solosko, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 771 days.

(21) Appl. No.: 09/796,381

(22) Filed: Feb. 28, 2001

(65) Prior Publication Data

US 2003/0017743 A1 Jan. 23, 2003

(51) Int. Cl.⁷ .................. H01R 13/52; B65D 81/124; A61B 5/04
(52) U.S. Cl. .................. 439/521; 206/205; 600/392
(58) Field of Search .................. 439/521; 206/205; 600/391, 392

(56) References Cited

U.S. PATENT DOCUMENTS

| 5,520,180 A | * | 5/1996 | Uy et al. ............. 600/397 |
| 5,607,454 A | | 3/1997 | Cameron et al. |
| 5,645,571 A | | 7/1997 | Olson et al. |
| 5,735,879 A | | 4/1998 | Gliner et al. |
| 5,827,314 A | * | 10/1998 | Lunsford et al. ............ 606/192 |
| 5,836,993 A | | 11/1998 | Cole |
| 5,879,374 A | | 3/1999 | Powers et al. |
| 5,969,223 A | * | 10/1999 | Nagai et al. ............. 73/1.06 |
| 5,984,102 A | * | 11/1999 | Tay ............. 206/701 |
| 6,048,640 A | * | 4/2000 | Walters et al. ............. 429/136 |

* cited by examiner

Primary Examiner—Chandrika Prasad
(74) Attorney, Agent, or Firm—Tony Piotrowski (57) ABSTRACT

A package stores at least one electrode pad having a lead. The package includes an interior for storing the pad, and includes a portion that is openable to allow removal of the package from the leads. For example, the openable portion of the package may include a sealed seam through which the lead extends. The operator can peel apart the seam to both open the package and free the package from the lead. Where the pad is a defibrillator electrode pad, the ability to quickly and easily free the package from the lead may save precious seconds during the rescue of a patient in cardiac arrest. For example, freeing the package from the lead typically allows the operator a fuller view of and easier access to the defibrillator and the patient, and eliminates a potential distraction.

35 Claims, 8 Drawing Sheets

ELECTRODE-PAD PACKAGE THAT IS REMOVABLE FROM AN ELECTRODE-PAD LEAD AND METHOD FOR OPENING THE PACKAGE

BACKGROUND OF THE INVENTION

1. Field of the Invention

The invention relates generally to packages for storing an electrode pad of a medical device such as an automatic or semi-automatic external defibrillator (AED), and more particularly to a package that comes free of the electrode-pad lead while or after one opens the package. In one embodiment of the invention, one peels apart the portion of the package seam through which the lead extends to free the package from the lead.

2. Description of the Prior Art

AEDs have saved many lives in non-hospital settings, and, as a result of advances in AED technology, the number of lives saved per year is rising. Typically, an AED analyzes a patient's heart rhythm and instructs an operator to administer an electrical shock to the patient if appropriate. For example, a shock can often revive a patient who is experiencing ventricular fibrillation (VF). Because older models of AEDs include only basic diagnostic and safety features, they are often difficult to operate. Therefore, only specially trained persons such as emergency medical technicians (EMTs) can use these older models to administer shocks to patients. Newer models, however, often include advanced diagnostic and safety features that allow minimally trained persons to administer shocks to patients. Consequently, more people are using AEDs to save lives.

Because a heart rhythm that responds to an electrical shock can cause permanent damage or death within a short time if left untreated, an AED operator should be able to set up and use an AED to shock a patient within seconds after the operator arrives at the scene. Statistically, for each minute that a person is in cardiac arrest and is not receiving cardiopulmonary resuscitation (CPR), his/her chance of survival decreases by 10%. And in most cases, there is no chance for resuscitation after 10 minutes. Unfortunately, many people do not know how to administer CPR. And, even in the best of circumstances, it can take a few minutes to retrieve the AED and a few additional minutes for the AED to diagnose and shock the patient. Therefore, even if the patient is discovered immediately, the operator often has little time to remove the defibrillator electrode pads from their package, attach the pads to the patient, connect the pads to the AED, and activate the AED without further decreasing the patient's chances of survival. Clearly, the faster the operator can set up and activate the AED, the more likely it is that the patient will survive.

One way to facilitate faster set up of an AED is to connect the pads to the AED before it is needed to revive a patient. Such pad pre-connection typically shortens the AED setup time by eliminating the operator steps of determining how to connect, and then connecting the pads to the AED. For example, one can store the AED with the pads pre-connected so that the AED will be ready when needed.

Figure 1:
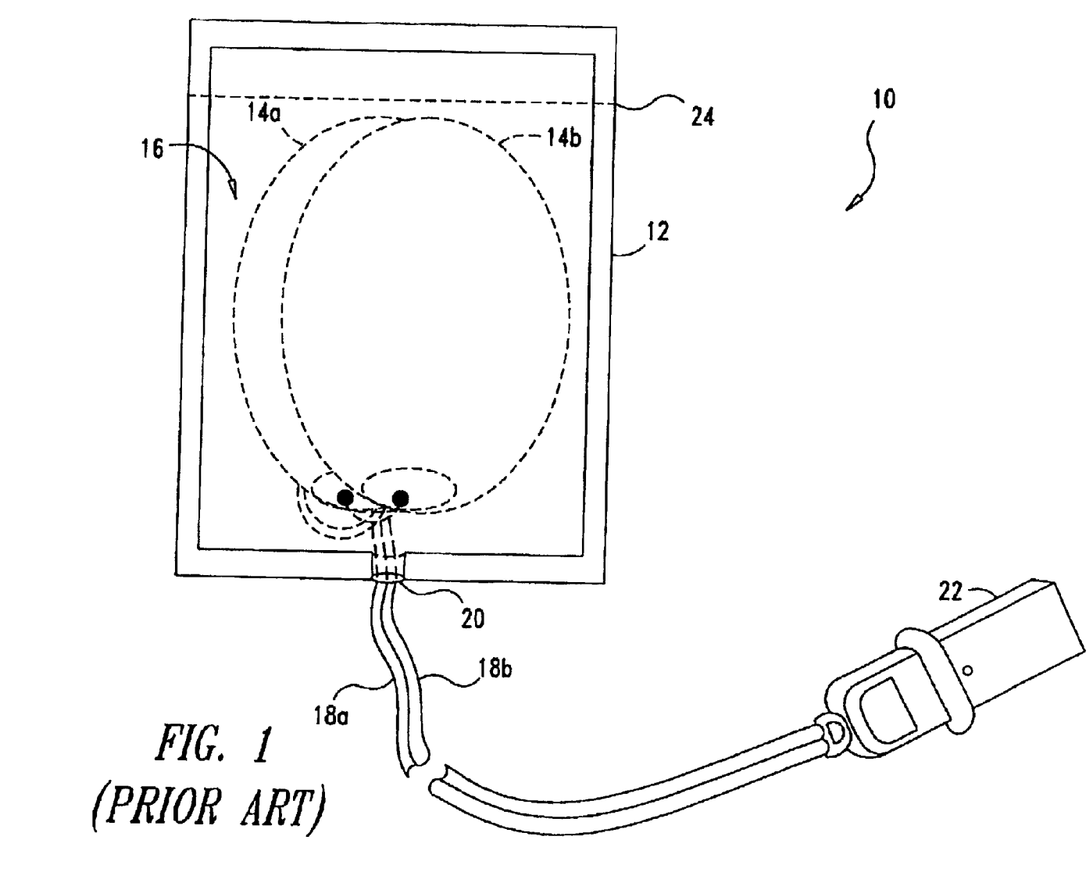
FIG. 1 is a view of a conventional electrode-pad storage system.
Figure 7:
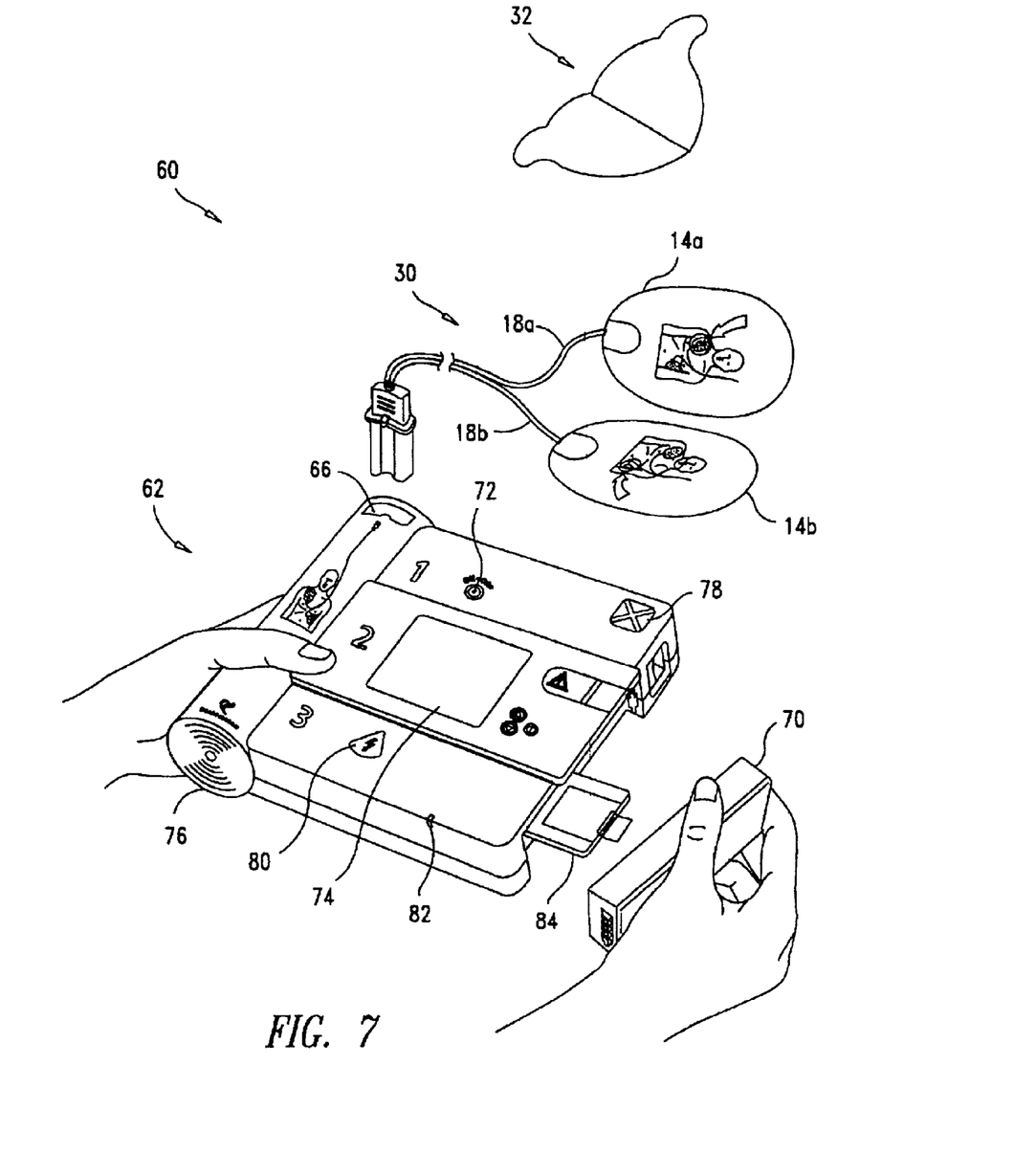
FIG. 7 is a view of an AED system that incorporates the electrode-pad storage system of FIGS. 3–4 or the system of FIGS. 5–6 according to an embodiment of the invention.

FIG. 1 is a view of a conventional defibrillator-electrode-pad storage system 10, which allows pre-connection of defibrillator electrode pads to an AED (FIG. 7). The system 10 includes a package 12 and two defibrillator electrode pads 14a and 14b (shown in phantom line) stored within an interior 16 of the package 12. Electrode-pad leads 18a and 18b extend from a sealed opening 20 in the package 12, and a connector 22 electrically connects the electrode pads 14a and 14b to the AED via the leads 18a and 18b. The package 12 may also include a tear line 24 to facilitate opening of the package. The rears of the pads 14a and 14b each include a conductive layer (not shown), which is typically coated with a contact gel (not shown). The gel provides electrical conduction between a patient (not shown) and the conductive layer and also helps adhere the pads 14a and 14b to the patient. Typically, a release liner is placed over the gel surface of each electrode to prevent the gel from adhering to the package or other electrodes. However, the electrode gel surfaces could also be adhered to the inside surfaces of the package or to a common release liner, shared by both electrodes. Typically, the pads 14a and 14b are viable only while the respective contact gels each maintain a respective moisture level that is at or above a predetermined threshold. Therefore, the package 12 typically limits moisture loss from the package interior 16 to a rate sufficient for maintaining adequate moisture in the contact gels for a predetermined period such as one year. The package 12 also protects the pads 14a and 14b from shipping and storage damage, and thus is often ruggedly constructed and reinforced around the opening 20.

During set up of the pre-connected AED, the operator (not shown) tears the top of the package 12 off at the tear line 24, removes the pads 14a and 14b from the package interior 16 via the torn-open top of the package 12, and attaches the pads 14a and 14b to a patient (not shown).

Figure 2:
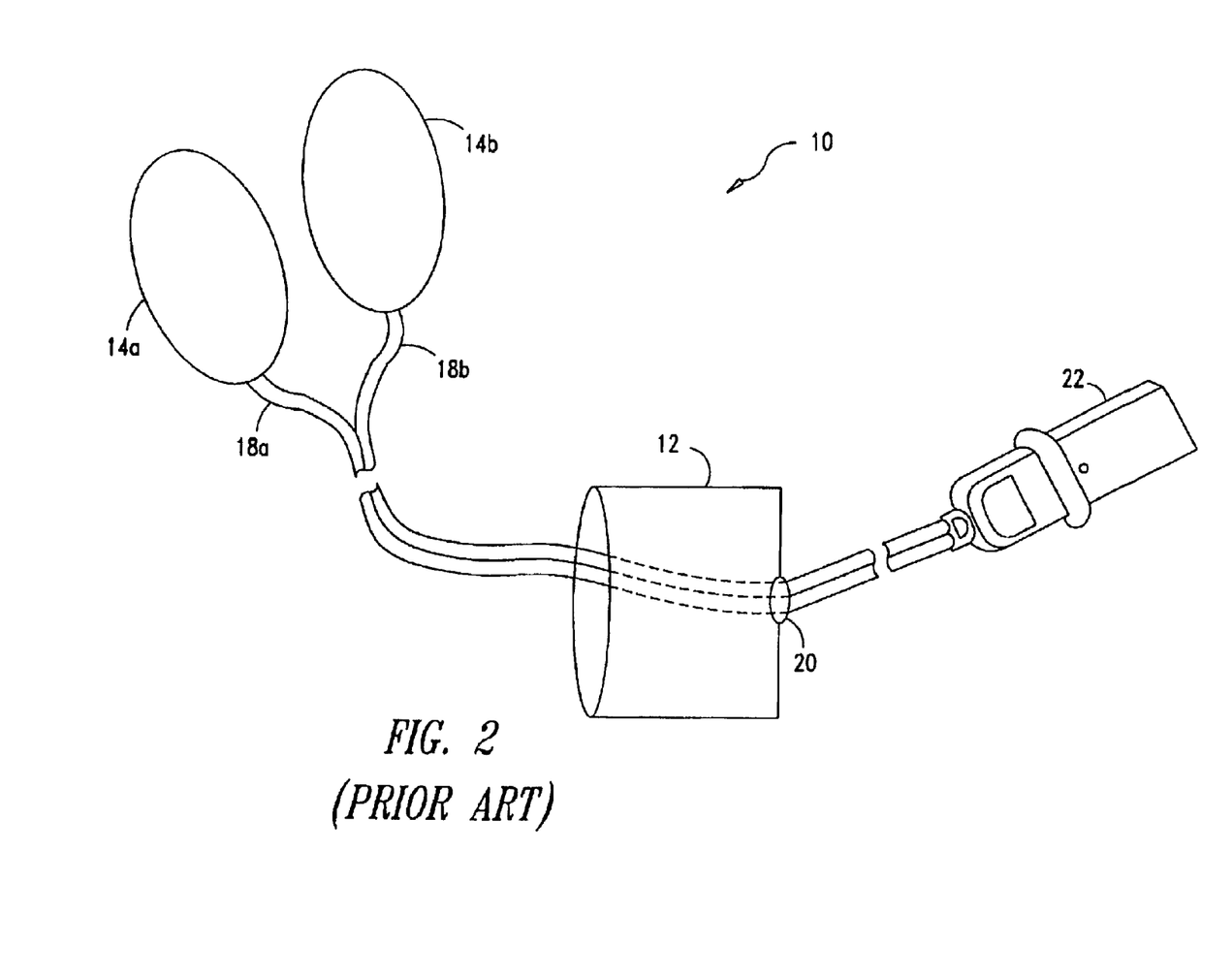
FIG. 2 is a view of the storage system of FIG. 1 with the pad package open but stuck to the pad leads.

Referring to FIG. 2, one problem with the defibrillator-electrode-pad storage system 10 is that after the operator (not shown) opens the package 12, it remains attached to the leads 18a and 18b, and thus may hinder the operator (not shown) as he/she attempts to revive the patient (not shown). For example, the package 12 may distract the operator, who may waste valuable seconds trying to remove the package from the leads 18a and 18b. Moreover, the package 12 may obscure the operator's view of the AED (FIG. 7) or the patient, or may get in the operator's way as he/she attempts to access the AED or the patient.

Unfortunately, it is often difficult and time consuming to remove the package 12 from the leads 18a and 18b. The package 12 is often ruggedly constructed and reinforced around the opening 20, it is typically difficult for an operator (not shown) to free the package 12 from the leads 18a and 18b. And although an operator may have the strength or a cutting tool (e.g., scissors) to free the package 12 from the leads 18a and 18b, this would typically waste valuable seconds of rescue time and possibly damage the leads. Furthermore, although an operator may have the strength or a tool to widen the opening 20 enough to slip the package 12 over the connector 22, he/she would have to disconnect the connector from the AED (FIG. 7) and thus lose the time saved by pre-connection.

Consequently, there is a need for a package that can be quickly and easily removed from the leads of electrode pads and that also protects and maintains the viability of the pads.

SUMMARY OF THE INVENTION

A package is provided for storing at least one electrode pad having a lead. The package includes an interior for storing the electrode pad, and includes a portion that is openable to allow removal of the package from the lead. For example, the openable portion of the package may include a sealed seam through which the lead extends. The operator can peel apart the seam to both open the package and free the package from the lead.

Because it has an openable portion that allows removal of the package from a lead, the package often reduces the time it takes for an operator to set up a medical device such as an AED and attach an electrode pad to a patient. For example, the ability to quickly and easily free the package from the lead may save precious seconds by allowing the operator a fuller view and easier access to the medical device and the patient, and by eliminating a potential operator distraction.

DESCRIPTION OF THE PREFERRED EMBODIMENTS

The following discussion is presented to enable a person skilled in the art to make and use the invention. Various modifications to the preferred embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein.

Figure 3:
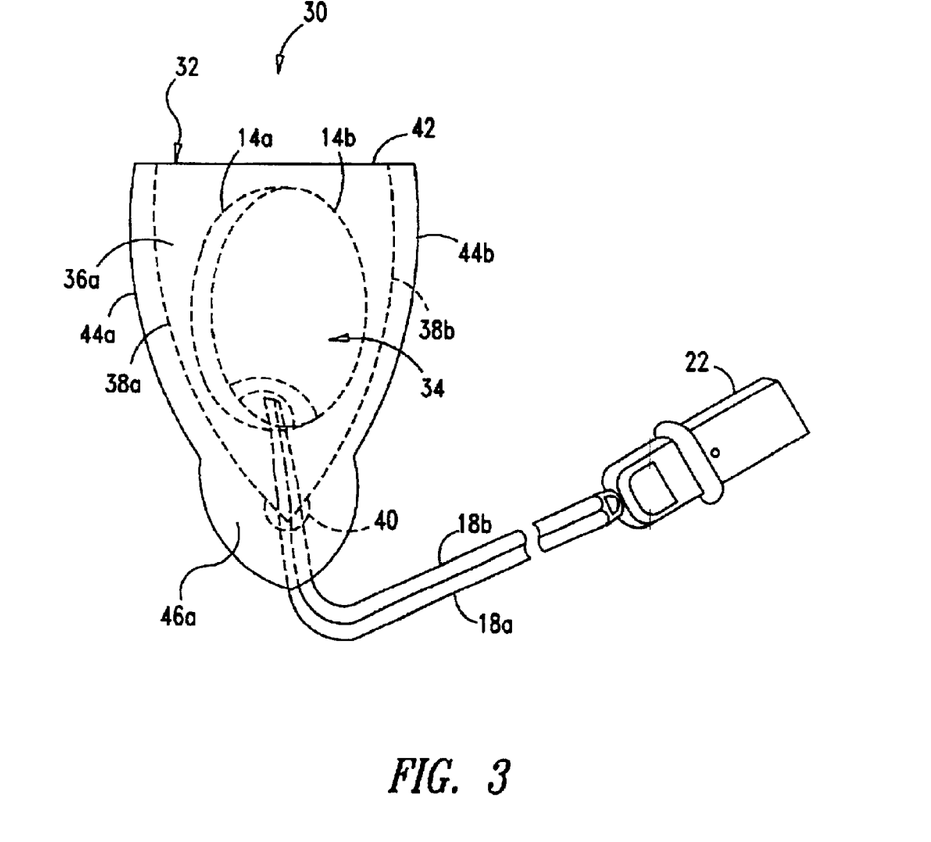
FIG. 3 is a view of an electrode-pad storage system according to an embodiment of the invention.

FIG. 3 is a view of an electrode-pad storage system 30, which includes a package 32 that an operator (not shown) can quickly and easily free from the pad leads 18a and 18b according to an embodiment of the invention. The system 30 also includes two defibrillator electrode pads 14a and 14b (shown in phantom line), electrode-pad leads 18a and 18b, and a connector 22, which are respectively similar to the pads 14a and 14b, leads 18a and 18b, and connector 22 of FIGS. 1 and 2.

The package 32 includes an interior 34 for holding the pads 14a and 14b, front and back sides 36a and 36b (FIG. 4), sealed seams 38a and 38b, a sealed opening 40 through which the leads 18a and 18b extend, a folded top edge 42, side edges 44a and 44b (FIG. 4), and pull tabs 46a and 46b.

The sides 36a and 36b of the package 32 are formed from a single piece of material that is folded together along the top edge 42 and that inhibits moisture loss from the interior 34 in the manner described above in conjunction with FIG. 1. Materials suitable for the sides 36a and 36b are known, and some are described in U.S. patent application Ser. No. 09/746,117, entitled "HALF CLEAR PACKAGE FOR USE WITH DEFIBRILLATION ELECTRODES", filed Dec. 22, 2000, which is incorporated by reference.

The sides 36a and 36b are sealed together along the seams 38a and 38b with a conventional adhesive that causes the sealed seams to inhibit moisture loss from the package interior 34 and yet allows an operator to quickly and easily peel the package 32 open. This is known as a peelable seal. The seams 38a and 38b follow the respective contours of the edges 44a and 44b, and thus taper toward and meet at the opening 40, which is also sealed with the adhesive to inhibit moisture loss from the interior 34. As discussed below in conjunction with FIG. 4, the taper of the seams 38a and 38b reduces the peeling force needed to open the package 32 as compared to the peeling force needed to open a package where portions of the seams 38a and 38b are parallel to the top edge 42.

The tabs 46a and 46b (FIG. 4) are respective integral extensions of the sides 36a and 36b. The tabs 46a and 46b are not sealed to one another; this allows an operator to grasp and pull apart the tabs to open the package 32 and to simultaneously free the package from the leads 18a and 18b.

Alternative embodiments of the electrode-pad storage system 30 are contemplated. For example, the sides 36a and 36b (FIG. 4) may be two separate pieces that are sealed together along a seam (not shown) that is adjacent to or aligned with the top edge 42. Furthermore, the opening 40 may be along this top-edge seam, along one of the seams 38a and 38b, or along a fourth seam (not shown) formed between the bottom (tab) ends of the seams 38a and 38b. Moreover, the seams 38a and 38b may be aligned with, and thus not overlapped by, the edges 44a and 44b. In addition, the edges 44a and 44b may have different contours—such as a non-tapered contour—than the seams 38a and 38b, respectively. Furthermore, the tabs 46a and 46b may be pieces of material (not shown) that are respectively attached to the sides 36a and 36b, and thus not integral extensions of the sides. Moreover, the sides 36a and 36b may be opaque or have see-through portions. In addition, there may be more or fewer than two defibrillator electrode pads 14a and 14b, or the electrode pads may be monitor (e.g., electrocardiogram, brainwave) pads or other types of pads. Furthermore, the entire lengths of the leads 18a and 18b, may be sealed inside of the package 32—the connector 22 may be inside or outside of the package—before the package is opened.

Figure 4:
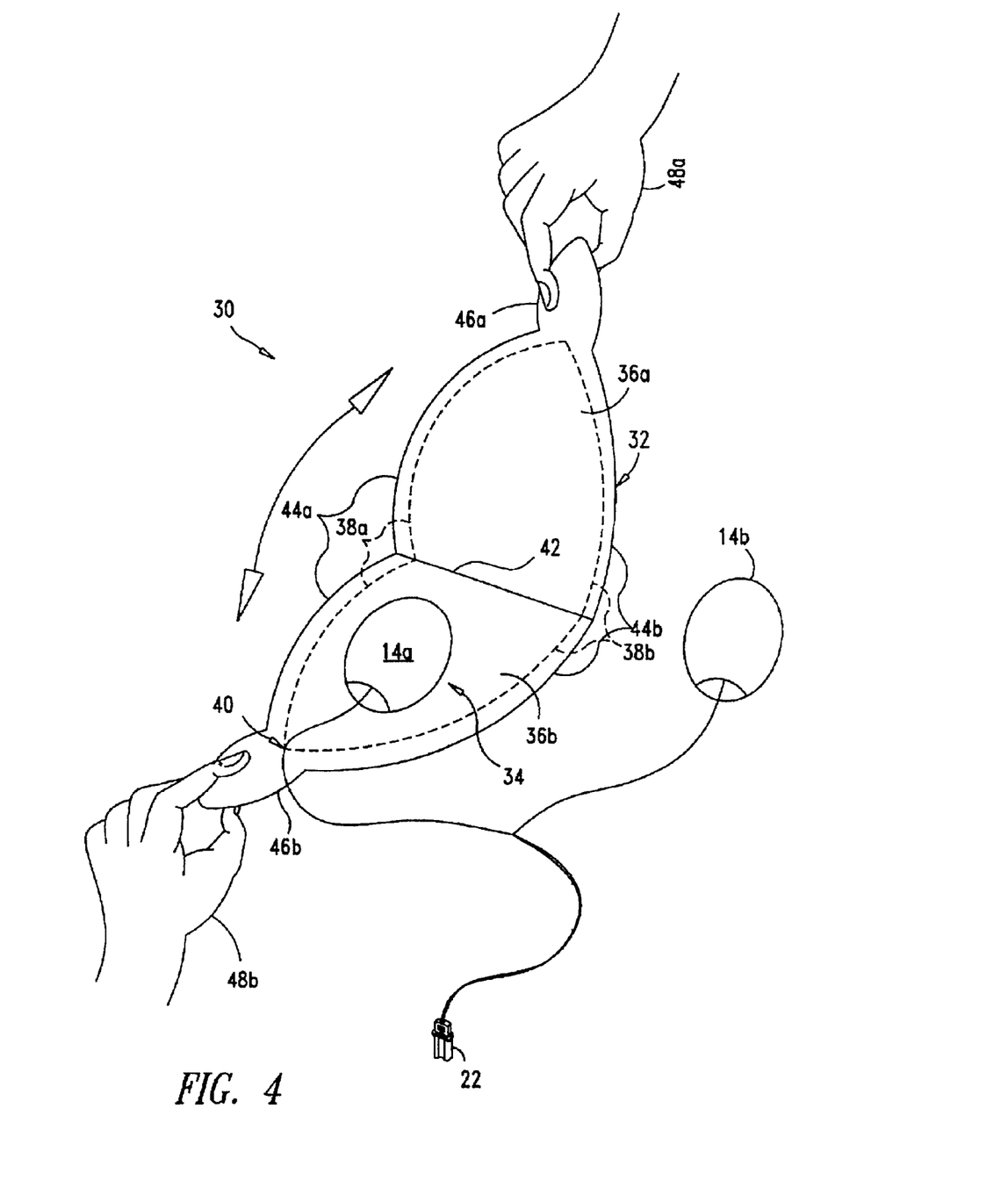
FIG. 4 is a view of the storage system of FIG. 3 with the pad package open.

FIG. 4 is a perspective view of the electrode-pad storage system 30 of FIG. 3 after an operator (hands 48a and 48b shown) has opened the package 32.

Referring to FIGS. 3 and 4, a procedure for opening the package 32 is described according to an embodiment of the invention. The operator first grasps the tabs 46a and 46b with, for example, the fingers of his respective right and left hands 48a and 48b. The operator may position his fingers as shown or in any other grasping position. Next, the operator pulls the tabs 46a and 46b apart (as indicated by the arrows) to open the package 32. Because the seams 38a and 38b are pulled apart along the region, i.e., the opening 40, through which the leads 18a and 18b extend, the leads are free of the package 32, particularly after the operator removes the pads 14a and 14b from the package.

The taper of the seams 38a and 38b makes it easier for the operator to open the package 32. Theoretically, there are two boundary points—one along the seam 38a, the other along the seam 38b—that the operator is peeling apart. i.e., separating, at any one time. A boundary point is the adhered point of a seam that is at the boundary between the separated and adhered portions of the seam. A unit of force—which is dependent, e.g., on the amount and strength of the adhesive, the width of the seam, and the taper angle of the seam—is needed to separate each boundary point. Although this unit of force may change from boundary point to boundary point, one can approximate by assuming that the same unit of force—a calculated mean unit for example—is needed to separate each boundary point. Therefore, the fewer boundary points that are being separated at any one time, the less force required to peel apart the package 32. By comparison, if the seams 38a or 38b have a portion that is parallel to the top edge 42, then the operator must separate more than two boundary points at a time, and thus pull apart the tabs 46a and 46b more forcefully, while peeling apart this parallel-seam portion. Consequently, although the package 32 can include such a parallel seam portion, opening such a package may be more difficult for the operator than opening a package with tapered seams.

Figure 5:
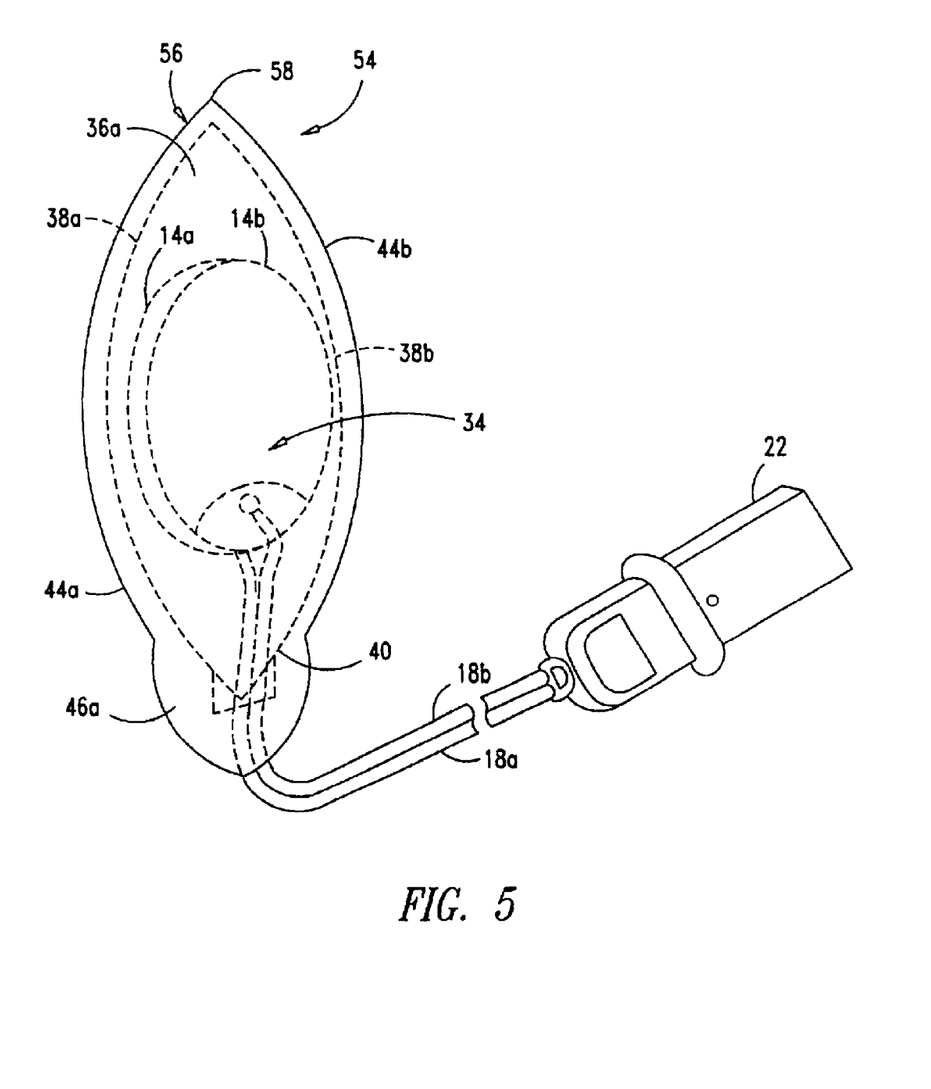
FIG. 5 is a view of an electrode-pad storage system according to another embodiment of the invention.

FIG. 5 is a view of an electrode-pad storage system 54, which includes a package 56 that an operator (not shown) can quickly and easily free from the pad leads 18a and 18b according to another embodiment of the invention. The system 54 also includes two defibrillator electrode pads 14a and 14b (shown in phantom line), electrode-pad leads 18a and 18b, and a connector 22, which are respectively similar to the pads 14a and 14b, leads 18a and 18b, and connector 22 of FIGS. 1–4. The package 56 includes an interior 34, front and back sides 36a and 36b, seams 38a and 38b, an opening 40, edges 44a and 44b, and tabs 46a and 46b, which are respectively similar to the like components of the package 32 of FIGS. 3 and 4.

A significant difference between the package 32 of FIGS. 3 and 4 and the package 56 is that the sides 36a and 36b are formed from two pieces of material—not from a single, folded piece of material like the sides 36a and 36b of the package 32. Together, the seams 38a and 38b extend all the way around the package interior 34, and are tapered toward the opening 40 in the bottom half of the package 56 and toward a top region 58 in the top half of the package.

The alternative embodiments discussed above in conjunction with FIGS. 3 and 4 for the electrode-pad storage system 30, as well as other alternative embodiments, are contemplated for the electrode-pad storage system 54.

Figure 6:
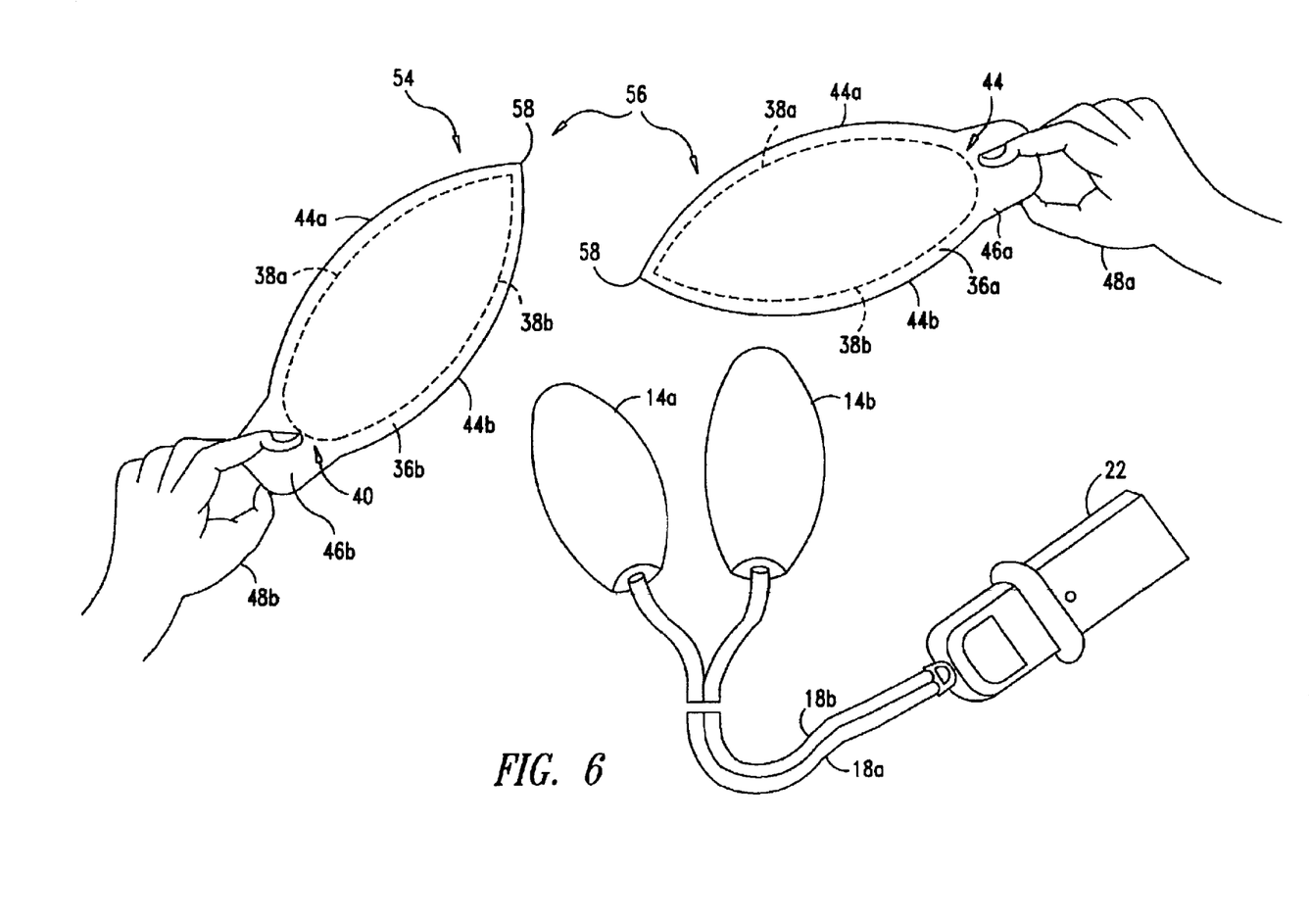
FIG. 6 is a view of the storage system of FIG. 5 with the pad package open.

FIG. 6 is a perspective view of the electrode-pad storage system 54 of FIG. 5 after an operator (hands 48a and 48b shown) has opened the package 56.

Referring to FIGS. 5 and 6, the procedure for opening the package 56 is similar to the procedure for opening the package 32 as described above in conjunction with FIGS. 3 and 4. Furthermore, the taper of the seams 38a and 38b makes it easier for the operator to open the package 56 as discussed above in conjunction with FIGS. 3 and 4.

FIG. 7 illustrates a general AED system 60, which includes an AED 62 for generating a shock and which includes the defibrillator-electrode-pad storage system 30 of FIGS. 3–4 or the system 54 of FIGS. 5–6 according to an embodiment of the invention. For clarity, the system 60 is discussed as including the electrode-pad storage system 30 of FIGS. 3–4, and the electrode pads 14a and 14b are shown removed from the opened package 32. The connector 22 couples the electrode pads 14a and 14b to a connector 66 of the AED 62. As discussed above in conjunction with FIGS. 1 and 2, the connector 22 may be pre-connected to the AED connector 66 to save time for the operator in an emergency. Otherwise, the operator can couple the connector 22 to the connector 66 before or after opening the package 32.

The AED 62 may include a battery 70 for supplying power, a main on/off key switch 72, a display 74 for displaying operator instructions, cardiac waveforms, or other information, a speaker 76 for providing audible operator instructions, an AED status indicator 78, and a shock button 80, which the operator presses to deliver a shock to the patient. The AED 62 may also include a microphone 82 for recording the operator's voice and other audible sounds that occur during the rescue, and a data card 84 for storing these sounds along with the patient's ECG and a record of AED events for later study.

Still referring to FIG. 7, during an emergency where it is determined that a patient (not shown) may need a shock, the operator retrieves the AED 62 and installs the battery 70 if it is not already installed. Next, the operator removes the defibrillator electrode pads 14a and 14b from the package 32 as discussed above in conjunction with FIGS. 3–4. Because it is free of the leads 18a and 18b, the package 32 can be discarded such that it does not distract the operator or obscure his view of or access to the AED 62 or the patient. If the connector 22 is not pre-connected, the operator inserts it into the connector 66. Then, the operator turns the on/off switch 72 to the "on" position to activate the AED 62. Following the instructions displayed on the display 74 or "spoken" via the speaker 76, the operator attaches the electrode pads 14a and 14b to the patient. After the operator attaches the electrode pads 14a and 14b to the patient, the AED 62 analyzes the patient's ECG to determine whether the patient is suffering from a shockable heart rhythm. If the AED 62 determines that the patient is suffering from a shockable heart rhythm, then the display 74 or the speaker 76 instructs the operator to depress the shock button 80 to deliver a shock to the patient. Conversely, if the AED 62 determines that the patient is not suffering from a shockable heart rhythm, the display 74 or the speaker 76 informs the operator not to shock the patient, and may inform the operator to seek appropriate non-shock treatment for the patient. Furthermore, when it informs the operator not to shock the patient, the AED 62 may disable the shock button 80.

Figure 8:
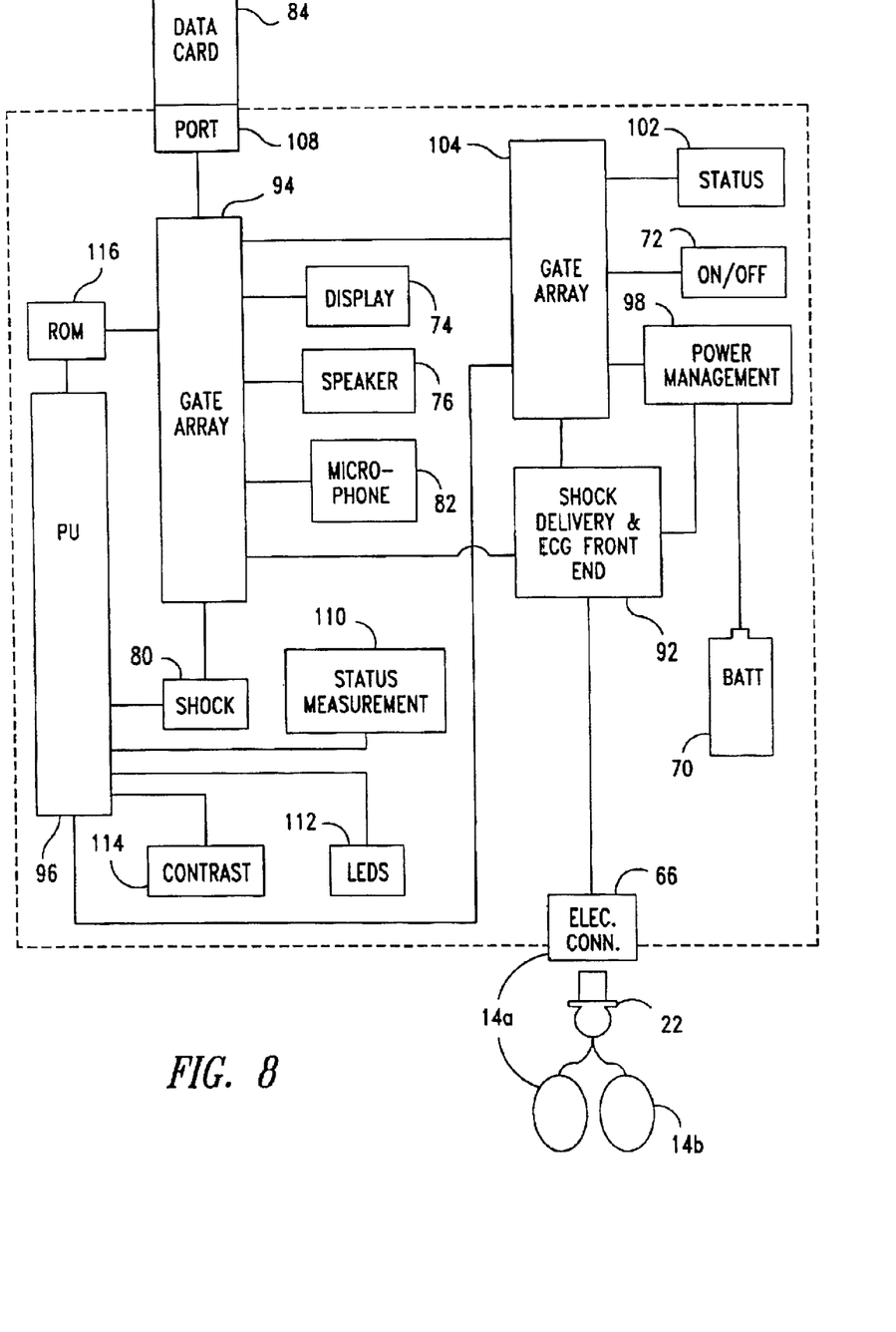
FIG. 8 is a block diagram of an AED circuit that the AED of FIG. 7 incorporates according to an embodiment of the invention.

FIG. 8 is a block diagram of an AED circuit 90, which the AED 62 of FIG. 7 can incorporate according to an embodiment of the invention. The defibrillator electrode pads 14a and 14b are coupled to the circuit 90 via the connectors 22 and 66 and are operable to sense a patient's ECG (not shown) and to apply an electrical shock to the patient (not shown). A shock-delivery-and-ECG front-end circuit 92 samples the patient's ECG during an analysis mode of operation and provides a shock to the patient via the connectors 22 and 66 and the electrode pads 14a and 14b during a shock-delivery mode of operation. A gate array 94 receives the ECG samples from the circuit 92 and provides them to a processor unit (PU) 96, which stores and analyzes the samples. If analysis of the patient's ECG indicates that the patient is suffering from a shockable heart rhythm, then the processor unit 96 instructs the circuit 92 via the gate array 94 to enable delivery of a shock when an operator (not shown in FIG. 8) presses the shock button 80. Conversely, if analysis of the patient's ECG indicates that the patient is not suffering from a shockable heart rhythm, then the processor unit 96 may disable the circuit 92 from delivering a shock to the patient.

Still referring to FIG. 8, the circuit 90 includes a power-management circuit 98 for distributing power from the battery 70 to the subcircuits of the circuit 90. The on/off switch 72 turns the circuit 90 "on" and "off", a status circuit 102 indicates the status of the circuit 90, and a gate array 104 interfaces the power-management circuit 98, the on/off circuit 72, and the status circuit 102 to the circuit 92, the processor unit 96, and the gate array 94. As discussed above in conjunction with FIG. 7, the display 74 displays information to an operator, the speaker 76 provides audio instructions to the operator, and the microphone 82 records the operator's voice and other audible sounds. The data card 84 is connected to the gate array 94 via a port 108. The card 84 stores the operator's voice and other sounds along with the patient's ECG and a record of AED events for later study. A status-measurement circuit 110 provides the status of the circuit 90 subcircuits to the processor unit 96, and LEDs 112 provide information to the operator such as whether the processor unit 96 has enabled the circuit 92 to deliver a shock to the patient. A contrast button 114 allows the operator to control the contrast of the display screen 74, and a memory such as a read only memory (ROM) 116 stores programming information for the processor unit 96 and the gate arrays 94 and 104.

The AED circuit 90 and other AED circuits are further discussed in the following references, which are incorporated by reference: U.S. Pat. No. 5,836,993, U.S. Pat. No. 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

What is claimed:

1. An electrode-pad storage system, comprising:
   an electrode-pad package comprising,
      an interior, and
      a seam that can be opened; and
   an electrode pad disposed in the interior, the electrode pad having a lead that extends through the seam of the package.

2. The electrode-pad storage system of claim 1 wherein the seam can be peeled apart to allow removal of the electrode pad from the interior of the package and the package from the lead.

3. The electrode-pad storage system of claim 1 wherein the electrode pad comprises a defibrillator electrode pad.

4. The electrode-pad storage system of claim 1 wherein the electrode pad comprises a monitor electrode pad.

5. The electrode-pad storage system of claim 1, wherein the seam is sealed to inhibit moisture loss from the interior.

6. The electrode-pad storage system of claims 1, wherein the seam is tapered toward the location where the lead extends through the seam of the package.

7. An electrode-pad storage system, comprising:
   an electrode-pad package comprising,
      a sealed seam which is designed to be opened to open the package,
      an opening disposed along the seam,
      first and second side portions attached to and separable from one another along the seam as the package is opened, and
      a package interior defined by the first and second side portions; and
   an electrode pad disposed in the package interior and having a lead that extends through the opening, which is sealed around the lead.

8. The electrode-pad storage system of claim 7 wherein the first and second sides respectively include first and second tabs that facilitate peeling apart the first and second sides along the seam.

9. The electrode-pad storage system of claim 7 wherein the first and second sides respectively include first and second tabs that are aligned with the opening and that facilitate peeling apart the first and second sides along the seam.

10. The electrode-pad storage system of claim 7, wherein the seam is sealed to inhibit moisture loss from the package interior.

11. An electrode-pad storage system, comprising:
    an electrode-pad package comprising,
       an opening,
       first and second seams that join the opening,
       first and second sides attached to and separable from one another along the first and second seams, and
       an interior disposed between the first and second sides; and
    an electrode pad disposed in the interior and having a lead that extends through the opening, which is sealed around the lead.

12. The electrode-pad storage system of claim 11 wherein the first and second sides respectively include first and second tabs that are aligned with the opening and that facilitate peeling apart the first and second sides along the first and second seams.

13. The electrode-pad storage system of claim 11 wherein the first and second seams taper toward the opening.

14. The electrode-pad storage system of claim 11 wherein the electrode-pad package further comprises:
    an edge that is contiguous with the first and second seams;
    wherein the first and second sides compose a piece of material that is folded along the edge; and
    wherein the first and second sides are peelable along the first and second sides from the opening toward the edge.

15. The electrode-pad storage system of claim 11 wherein the electrode-pad package further comprises:
    a region that is opposite the opening;
    wherein the first and second seams join the region;
    wherein the first and second sides are attached to and separable from one another along the region; and
    wherein the first and second sides are peelable along the first and second seams from the opening toward the region.

16. The electrode-pad storage system of claim 11 wherein the opening of the package is sealed to inhibit moisture loss from the interior of the package.

17. The electrode-pad storage system of claim 11, further comprising a connector coupled to the lead and disposed outside of the electrode-pad package.

18. The electrode-pad storage system of claim 11, wherein the first and second seams are sealed to inhibit moisture loss from the interior.

19. The electrode-pad storage system of claim 7, wherein the side portions are tapered toward the lead opening.

20. A defibrillator system, comprising:
    a defibrillator, and
    a defibrillator-electrode-Pad storage system, comprising
       a package comprising,
          an interior, and
          a sealed seam that can be peeled open, and
       a defibrillator electrode pad disposed in the interior and having a lead that extends through the sealed seam of the package,
       wherein peeling open the sealed seam enables the electrode pad to be removed from the interior and the package to be removed from the lead.

21. The defibrillator system of claim 20 wherein the defibrillator comprises a an automatic or semi-automatic external defibrillator.

22. The defibrillator system of claim 20 wherein:

the defibrillator comprises a first connector, and wherein the defibrillator-electrode-pad storage system comprises a second connector coupled to the lead and disposed outside of the package, the second connector attachable to the first connector.

23. The defibrillator system of claim 20, wherein seam is sealed to inhibit moisture loss from the interior.

24. The defibrillator system of claim 20, wherein the seam is tapered toward the location where the lead extends through the sealed seam of the package.

25. A method, comprising:

freeing an electrode-pad lead from a package by opening a portion of the package through which the electrode-pad lead extends; and removing an electrode pad from the package and the package from the electrode-pad lead.

26. The method of claim 25 wherein opening comprises opening a portion of a seam through which the lead extends.

27. The method of claim 25 wherein opening comprises separating the package along a portion of a seam through which the lead extends.

28. The method of claim 25 wherein opening comprises peeling apart the package along a portion of a seam through which the lead extends.

29. The method of claim 25, further comprising attaching the electrode pad to a patient after removing the electrode pad form the package.

30. The method of claim 25, further comprising attaching the electrode pad to a medical device after removing the electrode pad from the package.

31. The method of claim 25, further comprising attaching the electrode pad to a medical device before removing the electrode pad from the package.

32. The method of claim 25, further comprising:

wherein the electrode pad comprises a defibrillator electrode pad; and attaching the defibrillator electrode pad to a defibrillator before removing the defibrillator electrode pad from the package.

33. The method of claim 25, further comprising:

wherein the electrode pad comprises a defibrillator electrode pad; and attaching the defibrillator electrode pad to a defibrillator after removing the defibrillator electrode pad from the package.

34. A method, comprising:

freeing an electrode-pad lead from a package by peeling apart a portion of a package seam through which the electrode-pad lead extends; and removing a first electrode pad from the package and the package from the electrode-pad lead after peeling apart the portion of the package seam.

35. The method of claim 34, further comprising removing a second electrode pad from the package after peeling apart the portion of the package seam.

* * * * *